(12) United States Patent
Winkler

(10) Patent No.: US 7,077,924 B2
(45) Date of Patent: Jul. 18, 2006

(54) METHOD FOR PRODUCING TAPES IN PAIRS FOR THE MANUFACTURE OF CLOSING TAPES FOR DIAPERS

(75) Inventor: Michael E. Winkler, Cape Girardeau, MO (US)

(73) Assignee: Nordenia USA inc., Jackson, MO (US)

( * ) Notice: Subject to any disclaimer, the term of this patent is extended or adjusted under 35 U.S.C. 154(b) by 315 days.

(21) Appl. No.: 10/724,936

(22) Filed: Dec. 1, 2003

(65) Prior Publication Data

US 2005/0115663 A1 Jun. 2, 2005

(51) Int. Cl.
*A61F 13/56* (2006.01)
*A61F 13/62* (2006.01)

(52) U.S. Cl. ............... 156/201; 156/204; 156/259; 156/260; 156/264; 156/271

(58) Field of Classification Search ........... 156/201, 156/204, 227, 259, 260, 264, 461, 467, 512, 156/517, 519, 554, 269, 271
See application file for complete search history.

(56) References Cited

U.S. PATENT DOCUMENTS

| | | | |
|---|---|---|---|
| 5,595,618 A * | 1/1997 | Fries et al. ............. | 156/164 |
| 5,660,666 A * | 8/1997 | Dilnik et al. ............. | 156/259 |
| 6,471,152 B1 | 10/2002 | Suzuki et al. | |
| 2004/0188004 A1 * | 9/2004 | Guenther et al. .......... | 156/204 |

* cited by examiner

*Primary Examiner*—Sam Chuan Yao
*Assistant Examiner*—Barbara J Musser
(74) *Attorney, Agent, or Firm*—Collard & Roe, P.C.

(57) ABSTRACT

A method for producing tapes in pairs for the manufacture of closing tapes for baby diapers. The tapes are formed mirror-symmetrically and secured on the baby diapers in pairs. The method comprises the following steps: a web of material is separated in four strips, whereby two strips are processed as plane support tapes. The two other strips are guided via reversing stations over the support tapes and folded to form release tapes that each comprise a short leg and a long leg. Closing tapes that comprise male or female closing elements for a mechanical self-closure, are laminated to the support tapes in the direction of transport of these support tapes. The release tapes are applied to the support tapes in the direction of transport, whereby the short leg is glued to the support tape, and the long leg at least partly covers the closing tape that has been applied to the support tape. There is also a device for producing the tapes using the method described above.

8 Claims, 5 Drawing Sheets

METHOD FOR PRODUCING TAPES IN PAIRS FOR THE MANUFACTURE OF CLOSING TAPES FOR DIAPERS

BACKGROUND OF THE INVENTION

The invention relates to a method and a device for producing in pairs, closing tapes for baby diapers. The tapes are formed mirror-symmetrically and fastened on the baby diapers in pairs.

The closing tapes to be produced, comprise a support tape, on which a section of a closing tape and also a section of a release tape are secured. The closing tape comprises a set of male or female closing elements for a self-closure that is a hook and loop fastening closure or a Velcro® closure. The release tape is folded asymmetrically and comprises a long leg and a short leg, whereby the short leg is glued to the support tape, and the long leg is at least covers the closing tape that is applied to the support tape. With the outer surface of the release tape, the closing tape is fastened on the outer surface of the diaper that consists of a foil, wherein the end of the support tape having closing is free and seized by hand when the diaper is closed. Two closing tapes are always fastened on one diaper. These closing tapes are connected to a backward front section of the diaper on the left and right sides, and also have to be formed in a mirror-symmetrical manner.

In the course of the manufacture of the diaper, the closing tapes are separated from pre-fabricated strips that are processed in the form of wound material. These tapes for the closing tapes that have to be attached on the diaper in pairs have a mirror-symmetrical, layered structure. The manufacture of these tapes is the object of the invention.

SUMMARY OF THE INVENTION

The invention is based on the problem of providing a method, and device by means of which the tapes can be produced in pairs in the simplest possible manner. These tapes are required to produce the closing tapes that have to be connected to a diaper.

The object of the invention is a method for producing in pairs, tapes for the manufacture of closing tapes for baby diapers. These tapes are formed mirror-symmetrically, and are fastened on the baby diapers in pairs. The method comprises the steps of forming:

(a) a web of material that is separated in four strips, whereby two strips are then processed as flat support tapes;

(b) the two other strips are passed via reversing stations over the support strips and folded to release tapes that each comprise a short leg and a long leg.

(c) closing tapes comprising male or female closing elements for a mechanical self-closure are laminated to the support tapes in the direction of transport of the latter; and (d) The release tapes are applied to the support tapes in the direction of transport, whereby the short leg is glued to the support tape and the long leg covers at least partly, the closing tape that has been applied to the support tape.

According to the invention, the tapes that are required for the manufacture of closing tapes on baby diapers are produced in pairs with a mirror-symmetrical layer structure. In the process as defined by the invention, the support tapes and the release tapes applied to the support tapes are produced from one single web of material. Thus, only one feed of the closing tapes is required, which preferably comprise a self-adhesive back as well as a surface consisting of hook-shaped, male closing elements.

In a preferred embodiment of the invention, the web of material is separated in two outer strips and two inner strips, whereby the two outer strips are processed as support tapes, and the two inner strips are reversed and folded so as to form the release tapes.

The strips for the release tapes are passed via reversing stations that each comprise two reversing rollers, which are aligned transversely in relation to the direction of the web of the support tapes. The distance between the reversing rollers is variable and is adjusted so that the release tape and the associated support tape will merge downstream of the reversing station with the desired association. With the help of the reversing stations, it is thus possible to position the release tapes on the support tapes so that the finished tapes have a mirror-symmetrical layer structure.

In a preferred implementation of the method, an adhesive is applied to the web of material before this material is separated in strips.

The tapes produced according to the above method are usefully wound in rollers. To prevent the roll windings from sticking together, it is possible to apply a silicone coating to the underside of the material web from which the support tapes and the release tapes are produced.

The material webs and the support tapes are guided through at least two synchronously driven reversing rollers, whereby the rotational speed of at least one pair of the reversing rollers is controlled. By controlling the rotational speed, the reversing rollers of the second or downstream (viewed in the direction of the web) pair of reversing rollers is driven at a higher peripheral speed than the first pair of reversing rollers that is acting on the material web. The web of material is tensioned in this way between the pairs of reversing rollers.

The closing tapes and the release tapes are supplied to a section of the support tapes that is resting against the periphery of a first (viewed in the direction of the web) reversing roller of the pair of reversing rollers acting on the support tapes. The force of contact pressure require for the connection can be generated with contact pressure-exerting rollers that are arranged on the circumference of the reversing roller.

Finally, it is useful if weakening (or score) lines are provided in the material web, along which the release tapes can be folded.

The invention can also relate to a device for creating closing tapes from a web of material wherein these closing tapes are for use on diapers. The device can comprise an unwind stand for unwinding the web of material; and a plurality of reversing rollers for receiving the web of material as it rolls over and past the reversing rollers. Downstream of a first set of reversing rollers is at plurality of cutting blades for cutting the web of material into at least four different sections, with two sections forming support tapes and at least two sections forming release tapes. Downstream of the cutting blades is at least one rerouting roller for rerouting the release tapes away from the support tapes. There is also at least one folding device for folding the two release tapes.

There can also be at least one recombination station for recombining the at least two release tapes with the at least two support tapes. Upstream of the recombination station is at least one deflector roller for receiving a feed of a plurality of closure tapes wherein the plurality of closure tapes are coupled to the at least two support tapes at the recombination station.

BRIEF DESCRIPTION OF THE DRAWINGS

Other objects and features of the present invention will become apparent from the following detailed description considered in connection with the accompanying drawing which discloses at least one embodiment of the present invention. It should be understood, however, that the drawing is designed for the purpose of illustration only and not as a definition of the limits of the invention.

In the drawings, wherein similar reference characters denote similar elements throughout the several views.

DETAILED DESCRIPTION OF PREFERRED EMBODIMENTS

Figure 1:
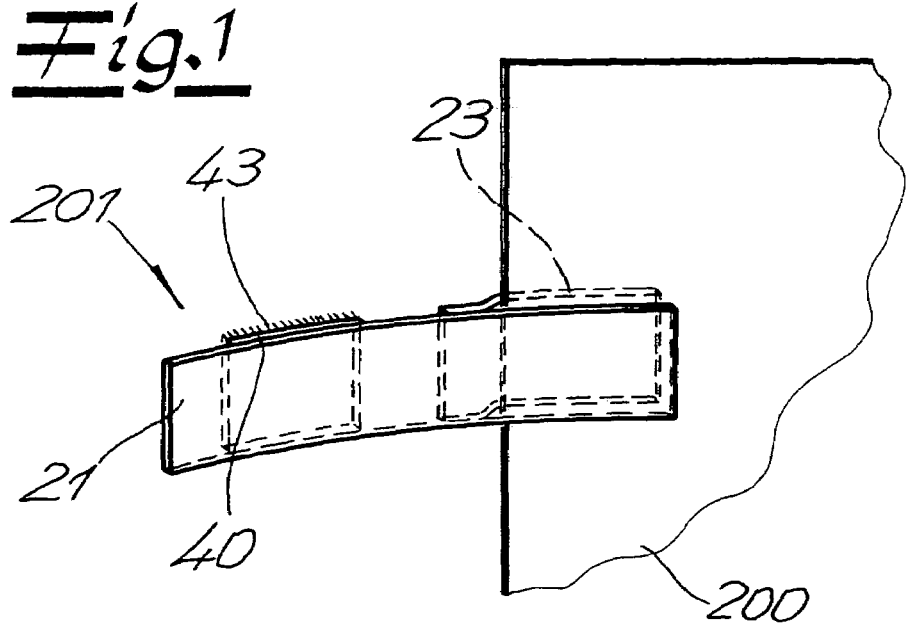
FIG. 1 shows a connection section of a baby diaper with a closing tape projecting sideways.
Figure 6:
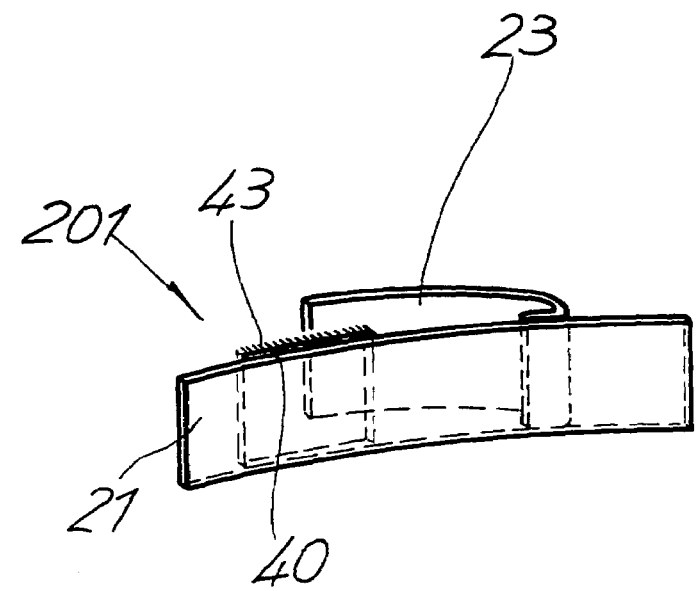
FIG. 6 shows one of the tapes produced with the device.

Turning now in detail to the drawings, FIG. 1 shows a closing tape 201, fastened on a baby diaper 200. As can be seen from FIG. 1 and FIG. 6, this closing tape comprises a support tape 21, 22. A section of a closing tape 40, 42 as well as a release tape 23, 24 are arranged on this support tape. Closing tape 40, 42 has male closing elements 43, which jointly with female closing elements of a counter piece, form a mechanical self-closure that is also referred to as a hook and loop fastener or a Velcro® closure. The end of support tape 21, 22 that closes tape 40, 42 can be seized by hand when diaper 200 is closed. Baby diaper 200 has a right and a left connection zone, with a closing tape 201 being fastened to each of these zones. Closing tapes 201 are separated from prefabricated strips that are produced on the device shown in the figures, using the method described in the following, and have a mirror-symmetrical layer structure.

Figure 2:
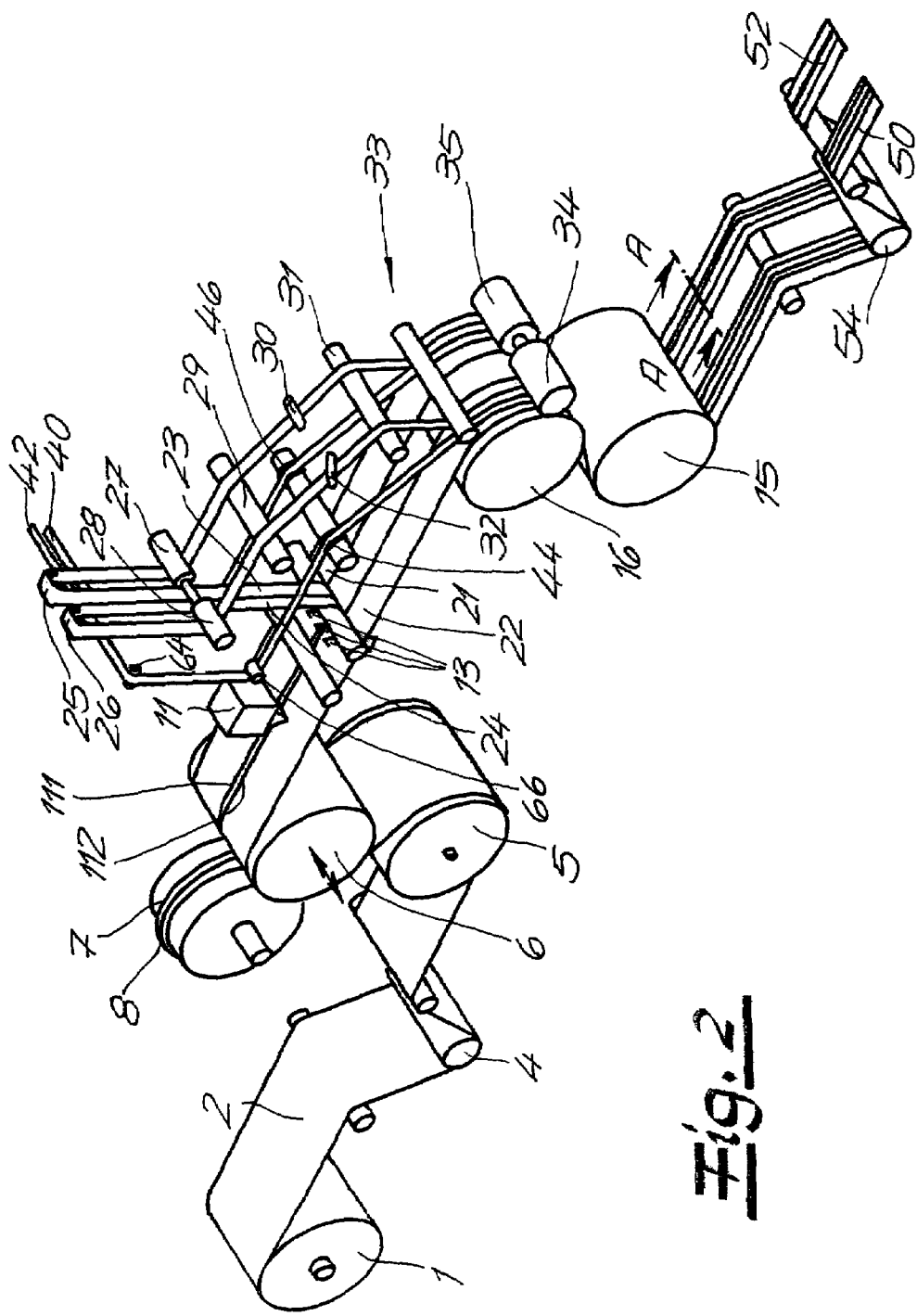
FIG. 2 shows under different aspects, a device for producing tapes in pairs for the manufacture of the closing tapes.
Figure 3:
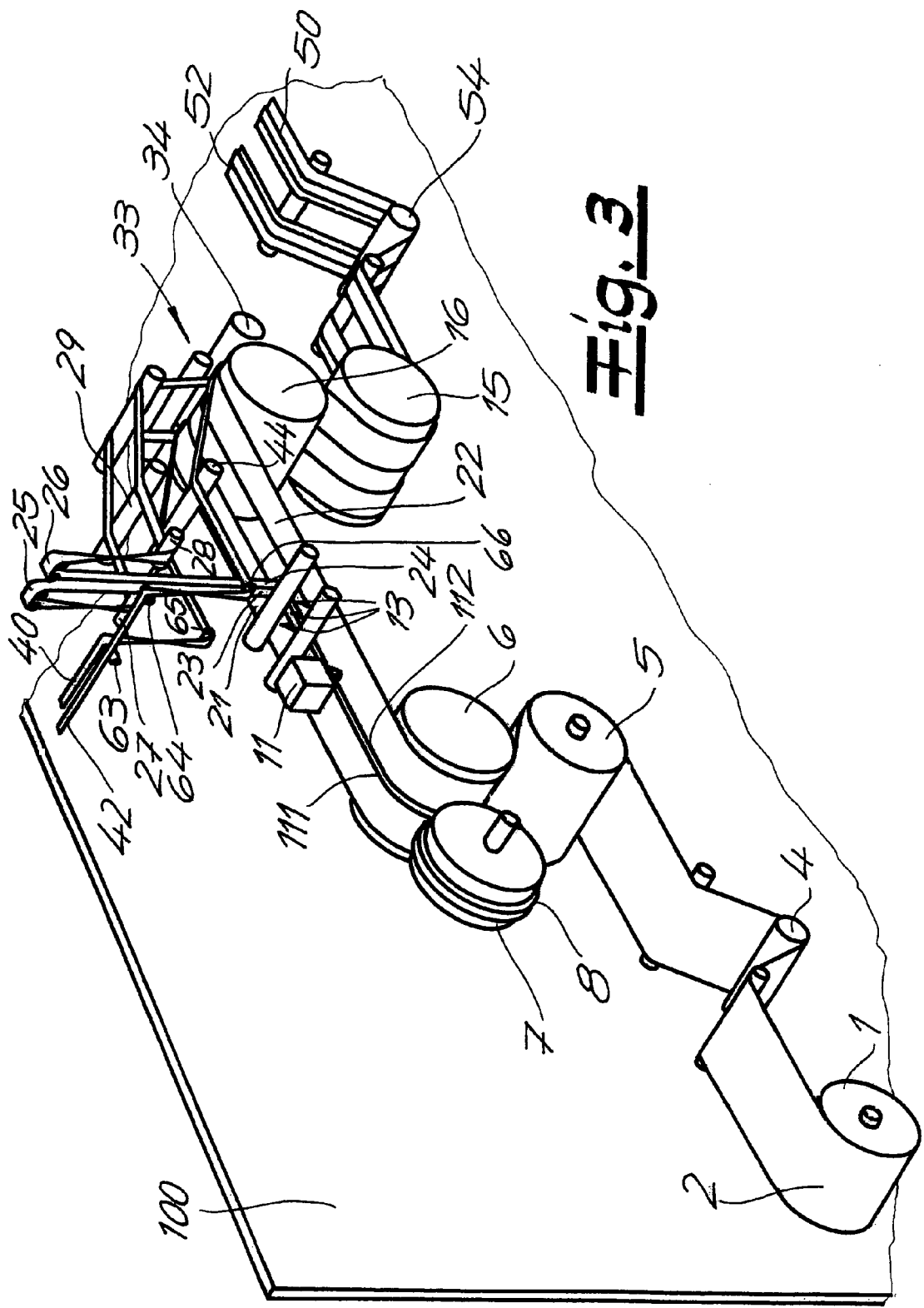
FIG. 3 shows under different aspects a device for producing tapes in pairs for the manufacture of the closing tapes.
Figure 4:
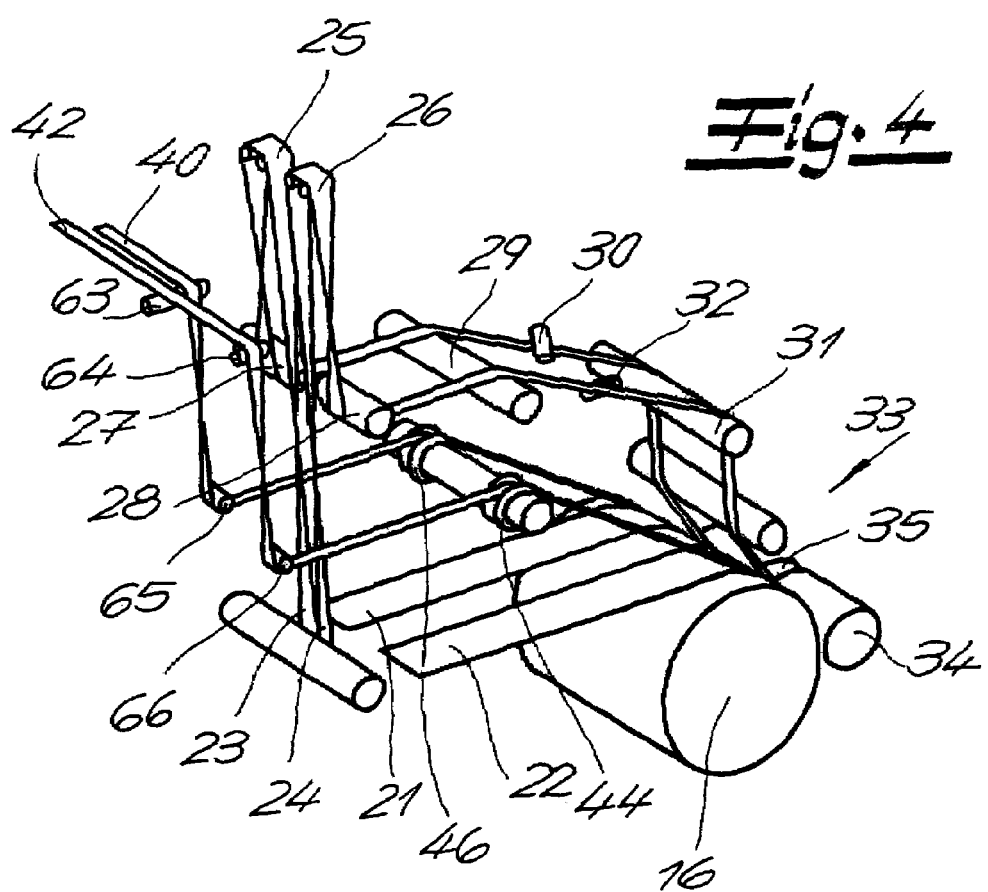
FIG. 4 is a cutout from the device shown in FIG. 3.

FIGS. 2, 3, 4 show a description of the parts of the apparatus for producing tape sandwich for right-and left-hand diaper ear fastening tabs. The different elements are mounted in front of a construction wall 100 (see FIG. 3), whereby the rollers and other transporting means are mounted on the front side. In this case, the driving elements, the motor and gears, are mounted on the backside and are therefore invisible.

The production line begins with the single driven unwind stand 1, which supplies a single web 2. The material of the web is a flexible polymer, e.g. polyethylene, of the same quality, stiffness and thickness as known in the art and ordered by the manufacturer of diapers. The width of web 2 is equal to 2 widths of a release tape, plus two widths of a fastening tape to be produced.

Web 2 is fed through a dancer roller feedback loop 4 to an arrangement of rollers 5 and 6. Dancer roller feedback loop 4 provides a controlled tension to web 2 before entering the serpentine path within the arrangement of rollers 5 and 6.

Web 2 is fed onto the periphery of roller 5, which is rubber-coated, and then onto the periphery of roller 6, which is a hardened steel roll with a low friction coefficient.

Furthermore, roller 6 is movable in the CD direction by a distance of about 10 mm. The CD direction is defined as a vector lying in the surface of the traveling web and has a direction at a right angle to the machine or traveling direction of the web.

The diameters of rollers 5 and 6 are essentially equal and are about 200 mm. Rollers 5 and 6 are connected by a gear to get equal rotational speed for both rollers. The gear is in the gearbox behind wall 10 and will not be visible. Both rollers 5 and 6 are driven by a DC motor set at an adjusted speed. The motor is not shown.

Second roller 6 also serves as an anvil roller for a set of two scoring rollers 7, 8, which are not driven, but entrained by roller 6 and loaded by an air pressure system (not shown) to be pressed on second roller 6. The scoring performed by scoring rollers 7, 8 is shown in FIGS. 2 and 3 by score lines 111 and 112 for folding the later release tape. For clarity, the scope lines are terminated and not shown beyond a certain point.

A second set of rollers 15, 16 with a similar diameter as rollers 5, 6 are positioned at a distance from the other set of rollers 5, 6. Rollers 15, 16 represent the other pillow support for the parts of web 2. Roller 16 is coated with an elastomer, whereas roller 15 is coated with steel sputtered by a plasma procedure.

Furthermore, the rotational speed between the set of rollers 15/16 and 5/6 is controlled by a differential gear (not shown), so that a differential speed is created. This differential speed is maintained by a variable, preset speed differential gear.

In the range between the sets of rollers 5/6 and 15/16, other important elements are situated. First, there is an adhesive applicator 11, which applies one or more types of adhesive, for example, melt blown polyethylene or other adhesives in one or more patterns depending on the product to be formed. The applied adhesive may come from a slot die, from a melt blown orifice, as it is used according to the customer's specification.

A set of three slitter blades 13 is arranged beneath the traveling web, which separates the web into four single tapes, which will become two fastening tapes 21, 22, and the two release tapes 23, 24. Release tapes 23, 24 are cut from a middle area of web 2, are then guided at a right angle from the web plane, and re-routed up to a pair of rerouting rollers 25, 26 for each tape. Release tapes 23 and 24 are then re-routed and shifted in the cross section, and then guided down via the three guiding rollers 27, 28 and 29.

Prior to a further guiding roller 31, a "Y"-bond is formed in the tapes 23 and 24, utilizing the scoring lines already scored into tapes 23 and 24. The folding is performed by the folding devices 30, 32. The folded tapes 23 and 24, are then guided to a recombination station 33 under the two air-pressured rollers 34, 35 pressed upon the surface of roller 16.

In addition to the tapes mentioned and made from the same web material of the web 2, an additional set of ribbons, for example, hook tapes 40, 42 are used. These hook tapes 40 and 42 are introduced into the process from an unwind unit (not shown), and are guided to the recombination station 33. Hook tapes 40, 42 are equipped with a very dense arrangement of hooks, which can engage a complementary piece of textile web to form a connection. Conversely, hook tapes 40, 42 can be in the form of loop tapes for receiving hooks from other hook tapes.

Hook tapes 40, 42 are fed from an unwind unit (not shown) over idler rollers 63 and 64, and are guided over deflector rollers 65, 66. The axis of rollers 63, 64, 65 and 66 are movable in the cross sections and align hook tapes 40, 42 in the proper cross direction relative to the fastening tapes 21, 22. Hook tapes 40, 42 are guided into the gap between fastening tapes 20, 21 and the release tapes 23, 24 at the recombination station 33, where they are placed into the correct position. Hook tapes 40, 42 are aligned into the correct position further by guiding collars 44, 46. Together with the three elements, there is formed a left-hand and a right-hand sandwich tape 50, 52.

After leaving the serpentine path between rollers 15 and 16, the left and the right sandwich tapes 50, 52 are passed over a common dancer roller system 54, which controls the upstream drive speed and tension of the sandwich tapes with the next work station (not shown) of the process. The sandwich tapes are rolled up on a drum or will be processed in a known manner.

Figure 5:
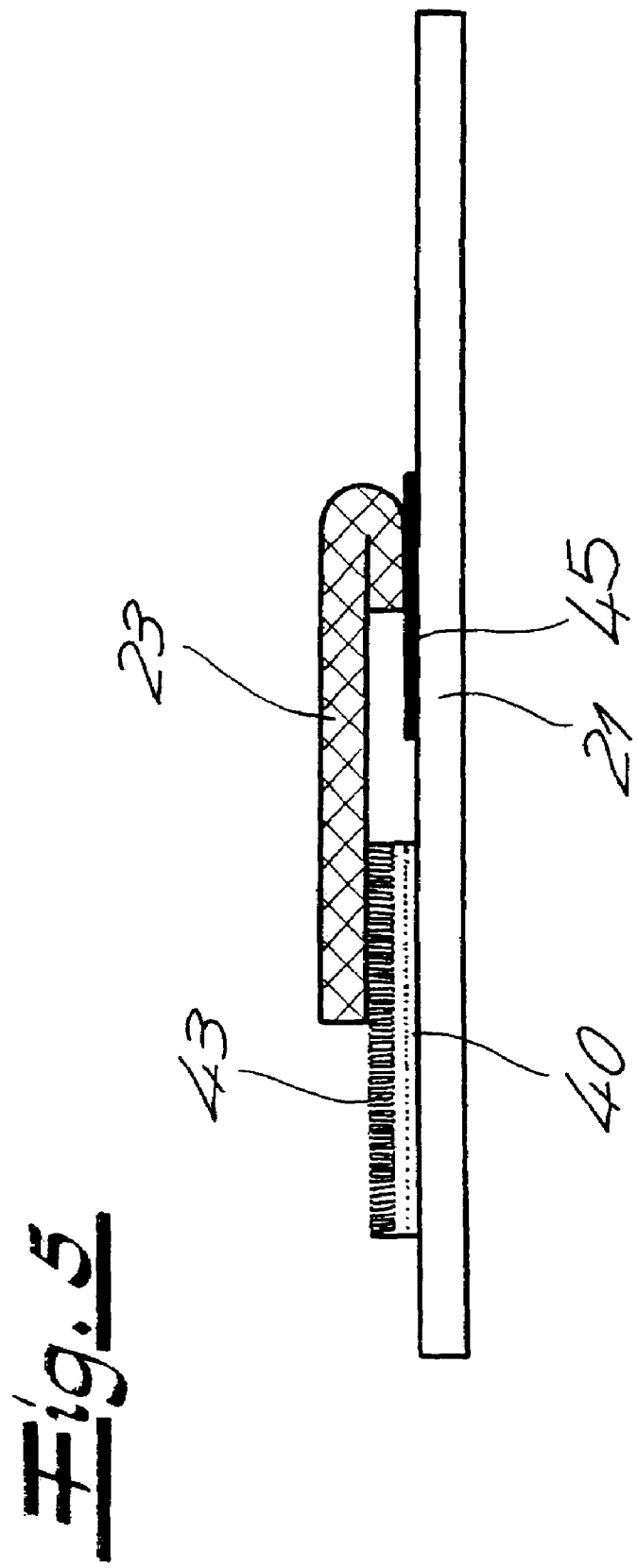
FIG. 5 is a cross section according to cut A—A in FIG. 2 through one of the tapes produced with the device.

Sandwich tapes 50, 52 as produced by the device according to the foregoing description are shown in FIG. 5. FIG. 5 shows a cross-section through tape 52 according to the line A—A in FIG. 2. The base of the laminate is formed by a broad web, which is fastening tape 21. Fastening tape 21 carries hook tape 40, which is self-adhesive on its downside bottom. Hooks 43 are located on the upper side. Release tape 23, which is bent in a hook-like form, has its main bend in the area of its score 111. The release tape 23 is fixed to the fastening tape 21 with a layer of glue 45. The release tape ends in an overlapping position on the hook tape 40, but without any fixed connected to this hook tape.

Tapes are produced in pairs with the device described above. These tapes have a mirror-symmetrical layer structure and can be processed further to closing tapes for baby diapers. The manufacturing process substantially comprises the following process steps: a web of material is separated in four strips, whereby two strips are processed as plane support tapes. The two other strips are guided via reversing stations over the support tapes and are folded to obtain release tapes. These release tapes each comprises a short leg and a long leg. Closing tapes that comprise male closing elements for a mechanical self-closure, are laminated to the support tapes in the direction of transport of these support tapes, whereby the short leg is glued to the support tape and the long leg at least partly covers the closing tape that has been applied to the support tape.

Adhesive is applied to the web of material before this web is separated into strips.

In the exemplified embodiment, the web of material used for the described method comprises a silicone coating applied to its underside.

Accordingly, while at least one embodiment of the present invention have been shown and described, it is to be understood that many changes and modifications may be made thereunto without departing from the spirit and scope of the invention as defined in the appended claims.

What is claimed is:

1. A method for producing tapes in pairs for a final set of manufactured closing tapes on baby diapers comprising the following steps:

a) separating a web of material into at least four strips wherein at least two of said strips are formed as planar support tapes and at least two of said strips are formed as release tapes;

b) guiding said at least two release tapes separate from said at least two support tapes over a plurality of reversing stations;

c) laminating in a direction of transport a set of closing tapes to said at least two support tapes, said set of closing tapes comprising male or female closing elements;

d) folding each of said at least two release tapes into a short leg and a long leg; and e) applying said release tapes to said support tapes in the direction of transport whereby said short leg is glued to said support tape and whereby said long leg at least partly covers said closing tape that is applied to said support tape.

2. The method as in claim 1, wherein the step of separating into four strips further comprises the step of separating said web of material into two outer strips and two inner strips, wherein said two outer strips are formed as said at least two support tapes and said two inner strips are said at least two release tapes.

3. The method as in claim 1, wherein said step of guiding said at least two release tapes comprises guiding said at least two release tapes via at least two reversing rollers which are aligned transversely in relation to the direction of transport of said at least two support tapes and wherein said at least two reversing rollers are spaced apart at a distance and set so that said at least two support tapes and said at least two release tapes merge in said step of applying said release tapes.

4. The method as in claim 1, further comprising the step of applying an adhesive to said web of material before said step of separating said web of material.

5. The method as in claim 1, wherein said web of material comprises a coating of silicone on an underside layer.

6. The method as in claim 3, further comprising the step of synchronously driving said at least two reversing rollers wherein a rotational speed of at least one of said reversing rollers is controlled, and wherein said web of material between said at least two reversing rollers is tensioned by said controlled speed.

7. The method as in claim 6, wherein said set of closing tapes and said at least two release tapes are applied to a section of said at least two support tapes resting in the direction of transport against a periphery of a first reversing roll of a pair of reversing rolls acting on the support tapes.

8. The method as in claim 1, further comprising the step of scoring said web of material, so that said step of folding said at least two release tapes includes folding said at least two release tapes along said scoring lines.

* * * * *